United States Patent [19]

Fawkes et al.

[11] Patent Number: 5,925,487
[45] Date of Patent: Jul. 20, 1999

[54] COMPOSITION, COMPOUND AND USE

[75] Inventors: David Melville Fawkes, Marple; Peter Gregory, Bolton; James Stanley Campbell, Manchester, all of United Kingdom

[73] Assignee: Zeneca Limited, London, United Kingdom

[21] Appl. No.: 08/860,491

[22] PCT Filed: Dec. 7, 1995

[86] PCT No.: PCT/GB95/02852

§ 371 Date: Jun. 27, 1997

§ 102(e) Date: Jun. 27, 1997

[87] PCT Pub. No.: WO96/20436

PCT Pub. Date: Jul. 4, 1996

[30] Foreign Application Priority Data

Dec. 28, 1994 [GB] United Kingdom ............... 942690

[51] Int. Cl.$^6$ .......... C03G 9/097; C03G 13/08; C07F 3/04; C07F 15/02
[52] U.S. Cl. .......... 430/120; 430/110; 430/137; 556/132; 556/148; 562/452; 562/467; 562/473; 562/475; 562/478
[58] Field of Search ................ 430/110, 120, 430/137; 524/286, 240, 291, 205; 562/473, 475, 478, 452, 467; 556/132, 148

[56] References Cited

U.S. PATENT DOCUMENTS

| 3,248,422 | 4/1966 | Elslager et al. |
|---|---|---|
| 3,983,292 | 9/1976 | Saito et al. ............................ 427/151 |
| 5,200,288 | 4/1993 | Ando et al. ............................ 430/110 |
| 5,230,977 | 7/1993 | Ohta ............................ 430/106 |
| 5,258,532 | 11/1993 | Lawson ............................ 556/132 |
| 5,301,037 | 4/1994 | Kang et al. ............................ 358/451 |
| 5,403,690 | 4/1995 | Kuramoto et al. ............................ 430/110 |

FOREIGN PATENT DOCUMENTS

| 0022701 | 1/1981 | European Pat. Off. ............... 524/291 |
|---|---|---|
| 463 876 | 1/1992 | European Pat. Off. . |
| 490 370 | 6/1992 | European Pat. Off. . |
| 490 508 | 6/1992 | European Pat. Off. . |
| 2006 916 | 6/1983 | Germany . |
| 7 301 343 | 10/1973 | Netherlands . |
| 1393854 | 5/1975 | United Kingdom . |
| 94/07842 | 4/1994 | WIPO . |

OTHER PUBLICATIONS

Derwent Abstract An 83–771423 of German Patent DD 200691 (Pub Jun. 1, 1983).

J. March, *Advanced Organic Chemistry: Reactions, Mechanisms, and Structure,* McGraw–Hill Book Co, NY (1968), p. 670.

N. Kondekar, et al. "Condensation of 3–Hydroxy–2–Naphthoic acid with formaldehyde", Industrial and Engineering Chemistry: Product Research and Development, 1973, pp. 135–137.

*Primary Examiner*—Janis L. Dote
*Attorney, Agent, or Firm*—Pillsbury Madison & Sutro Intellectual Property Group

[57] ABSTRACT

A toner resin composition comprising a toner resin and the metal salt or complex of a carbocyclic hydroxy caboxylic acid containing at least one methylene group optionally substituted by hydroxy or amino such as 4-(N-methyl-N-2-hydroxyethyl)aminomethyl-3-hydroxy-2-naphthoic acid. Iron and zinc salts are preferred.

12 Claims, No Drawings

COMPOSITION, COMPOUND AND USE

This application is the national phase of international application PCT/GB95/02852, filed Dec. 7, 1995 which was designated the U.S.

The present invention relates to a composition comprising a toner resin and an aromatic carbocyclic hydroxy carboxylic acid (hereinafter "AHCA") containing at least one methylene group optionally substituted by hydroxy or optionally substituted amino (hereinafter "AHCAM") including salts and metal complexes thereof and the use of such compounds as negative charge control agents. Some of the compounds are novel.

EP 490370 discloses metal salts and complexes of pamoic acid and their use as negative charge control agents.

EP 490508 discloses compounds having a fused aromatic ring system having hydroxy, carboxy and hydroxyalkyl substituents such as 3hydroxy-4-hydroxymethyl-2-naphthoic acid including salts and metal complexes thereof and their use as corrosion inhibitors. It has now been found that such compounds and derivatives thereof are useful as negative charge control agents (hereinafter "CCA") in electroreprographic imaging processes.

Thus, according to the invention there is provided a toner resin composition comprising a toner resin and an AHCAM including salts and metal complexes thereof with the exception of pamoic acid.

The carboxylic acid group is preferably attached to a carbon atom adjacent to that carrying the hydroxy group in the AHCA.

The AHCA may be a single aromatic ring which is preferably a phenyl ring as in salicylic acid and derivatives thereof or the AHCA may have one or more rings fused to a carbocydic aromatic ring which may contain 5 or 6 atoms and may be saturated or unsaturated and may be carbocyclic or heterocyclic. Preferred examples of such compounds contain two rings, particularly those where the fused ring contains 6 atoms as in naphthalene, tetrahydronaphthalene, quinoline and tetrahydroquinoline. Specific examples of such AHCA's include 2-hydroxy-1-naphthoic, 1-hydroxy-2-naphthoic and 8-hydroxy-1-naphthoic acids and especially 3-hydroxy-2-naphthoic acid.

The AHCAM is obtainable by reacting the AHCA with formaldehyde optionally in the presence of a primary or secondary amine. Under such conditions the methylene group is located in the ortho- and/or para-position to the hydroxy group in the AHCA.

Preferably the AHCAM contains the one methylene group and it is also preferred that such methylene group is in the ortho position relative to the hydroxy group of the AHCAM According to one aspect of the invention there is provided a composition comprising a toner resin and a AHCAM of formula 1

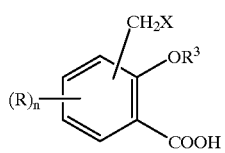

1 or a salt or metal complex thereof
wherein

X is hydroxyl, —NR$^1$R$^2$ or a group of formula 2

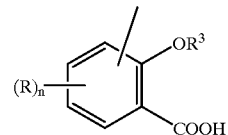

2

R is halogen, hydroxy, nitro, carboxy, nitrdle, optionally substituted C$_{1-18}$-hydrocarbyl or two adjacent groups R together with the carbon atoms to which they are attached form an optionally substituted 5- or 6-membered fused ring;

n is 0 to 3;

R$^1$ and R$^2$ is each, independently, hydrogen or optionally substituted C$_{1-18}$-hydrocarbyl or R$^1$ and R$^2$ together with the nitrogen atom to which they are attached form a ring; and R$^3$ is hydrogen, aralkyl or optionally substituted C$_{1-18}$-alkyl with the exception of pamoic acid.

Preferably, R$^1$ and R$^2$ are not both hydrogen.

When R, is hydrocarbyl it can be alkyl, alkenyl, alkynyl, aralkyl or aryl.

When R$^1$ and R$^2$ is hydrocarbyl it can be alkyl, cycloalkyl, aralkyl or aryl.

When R, R$^1$, R$^2$ or R$^3$ is alkyl, it may be linear, branched or alicyclic and is preferably C$_{1-12}$-alkyl, more preferably C$_{1-8}$-alkyl and especially C$_{1-6}$-alkyl. Examples of such groups include methyl, ethyl, propyl, n-butyl, i-butyl, n-hexyl, i-hexyl, 2-ethylbutyl, 2-ethylhexyl, nonyl, dodecyl, octadecyl and cyclohexyl.

When R is alkenyl it is preferably C$_{3-6}$-alkenyl.

When R, R$^1$, R$^2$ or R$^3$ is aralkyl it is preferably benzyl or 2-phenylethyl.

When R, R$^1$ or R$^2$ is aryl it is preferably phenyl.

When R, R$^1$ or R$^2$ is substituted hydrocarbyl, or when R$^3$ is substituted alkyl, the substituent or substituents is preferably at least one of hydroxy, carboxy, halogen or nitrile or the hydrocarbyl groups may contain a divalent atom or group such as

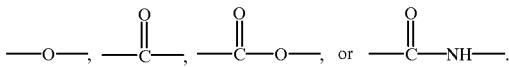

The preferred substituent in R,R$^1$, or R$^2$ is hydroxy.

When R is substituted hydrocarbyl it can also be another group —CH$_2$X, especially —CH$_2$NR$^1$R$^2$.

When R is or contains halogen or when R$^1$, R$^2$ or R$^3$ contains halogen, it is preferably fluorine, bromine and particularly chlorine.

When two adjacent groups R together with the carbon atoms to which they are attached form a fused ring, the fused ring is preferably phenyl as in naphthalene which may be substituted as described for R.

When R$^1$ and R$^2$ together with the nitrogen atom to which they are attached form a ring the ring preferably contains 6 atoms as for example morpholinyl, piperidinyl, piperazinyl and N—(C$_{1-6}$-alkyl)piperazinyl.

It is preferred that R is unsubstituted alkyl or two adjacent groups R together with the carbon atoms to which they are attached form a fused phenyl ring optionally substituted by alkyl groups.

In one preferred embodiment, n is zero and the AHCAM is a derivative of salicyclic acid.

In a further preferred embodiment, two adjacent groups R together with the carbon atoms to which they are attached form a fused ring, especially a fused phenyl ring as in naphthalene. It is particularly preferred that the naphthalene ring contains no substituents R.

The groups $R^1$, $R^2$ and/or $R^3$ are selected primarily to improve the compatibility of the AHCAM with the toner resin with which they are formulated. Thus, the size and length of the groups $R^1$ to $R^3$ may be selected to improve the physical entanglement or intercolation of the AHCAM with the resin or they may contain reactive entities capable of reacting chemically with the resin.

Preferably, $R^1$, $R^2$ and/or $R^3$ is or contains a saturated aliphatic chain and it is particularly preferred that the total number of carbon atoms is greater than four and preferably greater than 10. Preferably, the total number of aliphatic carbon atoms in $R^1$, $R^2$, and/or $R^3$ is less than 30, more preferably less than 24 and especially less than 18.

It is also preferred that $R^1$ is unsubstituted hydrocarbyl and especially unsubstituted alkyl.

In one preferred embodiment $R^3$ is hydrogen.

In a particularly preferred embodiment, the AHCAM is present as a salt or metal complex. The salt may be that of a primary, secondary or tertiary amine or a quaternary ammonium compound (hereinafter QAC). Preferred amines or QAC's are those containing $C_{1-24}$-alkyl chains, particularly where the alkyl chain contains more than 6 and especially more than 10 carbon atoms since these amines or QAC's are less volatile and are more resistant to the high temperature employed in the fabrication of toner resin compositions. Examples of amines and QAC cations are dodecylamine, octadecylamine, didecylamine, didodeceylamine, tetradecylamine, dodecylamine, hexadecylamine, $C_{12-18}$-mixed alkylamines and their N—$C_{1-6}$-alkyl or N,N-di-$C_{1-6}$-alkyl derivatives or N-benzyl derivatives, and particularly their methyl or ethyl derivatives, and N,N-diethyl-N-dodecyl-N-benzylammonium; N,N-dimethyl-N-octadecyl-N-(dimethylbenzyl)ammonium; N,N-dimethyl-N,N-didecylammonium; N,N-dimethyl-N,N-didodecylammonium; N,N,N-trimethyl-N-tetradecylammonium; N-benzyl-N,N-dimethyl-N-($C_{12-18}$-1-alkyl)ammonium; N-(dichlorobenzyl)-N,N-dimethyl-N-dodecylammonium; N-hexadecylpyridinium; N-hexadecyl-N,N,N-trimethylammonium; dodecylpyridinium; N-benzyl-N-dodecyl-N,N-bis(hydroxyethyl)ammonium; N-dodecyl-N-benzyl-N,N-dimethylammonium; N-benzyl-N,N-dimethyl-N-($C_{12-18}$-alkyl)ammonium; N-dodecyl-N,N-dimethyl-N-(1-naphthylmethyl)ammonium and N-hexadecyl-N,N-dimethyl-N-benzylammonium cations.

In an especially preferred embodiment the AHCAM is present as a salt or complex of a mono-, di- or trivalent metal. Preferred metals are those of groups 1a, 2a, 3a, 1b, 2b, 6b, 7b, and 8 of the Periodic Table according to Mendeleef as for example published in the inside rear cover of the Handbook of Chemistry and Physics published by The Chemical Rubber Co, Ohio, USA. Especially preferred metals are Mg, Ca, Ba, Cr, Mn, Fe, Co, Ni, Cu, Zn and Al. Metal salts or complexes derived from Mg(II), Ca(II), Ba(II), Zn(II) and Al(III) have the specific advantage that they are substantially colorless and such compounds may be used as CCA's for making colored images whereas compounds derived from Cr(III) and Fe(III) tend to be strongly colored and hence such CCA's are mainly of use for forming black images.

The salt or complex of the AHCAM can include more than one cation. Thus, it may comprise more than one metal or a combination of a metal together with an amine or QAC such that the salt or complex is a neutral molecule. It is preferred, however, that the salt or complex of the AHCAM is that of a metal.

The toner resin is a thermoplastic resin suitable for use in the preparation of toner compositions. A preferred toner resin is a styrene or substituted styrene polymer or copolymer such as polystyrene or styrene-butadiene copolymer.

It is especially preferred that the toner resin is a styrene-acrylic copolymer such as a styrene-butyl methacrylate copolymer. Other suitable toner resins are polyesters, especially alkoxylated bis-phenol based polyester resins such as those described in U.S. Pat. No. 5,143,809, polyvinyl acetate, polyalkenes, poly(vinyl chloride), polyurethanes, polyamides, silicones, epoxy resins and phenolic resins. Further examples of these and other resins are given in the book "Electrophotography" by R. M. Shafert (Focal Press); UK 2,090,008, U.S. Pat. No. 4,206,064 and U.S. Pat. No. 4,407,924.

The toner resin composition may contain more than one AHCAM. The ACHAM is preferably present in the composition from 0.1 to 12%, more preferably from 0.5 to 10% and especially from 1 to 3% by weight of the total composition.

The toner resin composition may also contain a dyestuff or pigment as colorants. Thus, according to a further aspect of the invention there is provided a toner resin composition as hereinbefore defined which further comprises a colorants. The colorants is preferably a pigment such as carbon black; magnetite; or a metallised phthalc-cyanine, quinacridone, perylene, benzidine, nigrosine, aniline, quinoline or anthraquinone pigment; or an azo disperse dye, benzodifuranone, metallised lake or pigment toner or water insoluble salt of a basic dye, including mixtures thereof. The colorants may also be a water soluble basic dye, especially a triphenylmethane dyestuff. The toner composition may contain up to 20% colorants and especially from 3 to 10% relative to the total weight of the toner resin composition.

When the colorant comprises magnetites or a mixture of magnetites and colored pigment the colorants is preferably present from 5 to 70% and more preferably from 10 to 50% by weight of the toner resin composition. Mixtures of carbon black and magnetite are available commercially and those containing from about 1 to 15% are preferred, especially those containing from 2 to 6% carbon black based on the weight of carbon black and magnetite.

The toner resin composition may be prepared by any method known to the art which typically involves mixing the toner resin with the AHCAM and optionally the colorants by kneading in a ball mill above the melting point of the resin. Generally, this involves mixing the molten composition for several hours at temperatures from 120 to 200° C., in order to uniformly distribute the AHCAM and colorants (if present) throughout the toner resin. The toner resin is then cooled, crushed and micronised until the mean diameter of the particles is preferably below $20\mu$ and, for high resolution electroreprography, more preferably from 1 to $10\mu$. The powdered colour toner or toner-resin so obtained may be used directly or may be diluted with an inert solid diluent such as fine silica by mixing for example in a suitable blending machine.

As noted hereinbefore many of AHCAM's including the salts and or metal complexes thereof, are new.

Thus, according to a still further aspect of the invention there is provided a AHCAM obtainable by reacting a AHCA with formaldehyde optionally in the presence of an amine, including a salt or metal complex thereof with the exception of 4-hydroxymethyl-3hydroxy-2-naphthoic acid and pamoic acid.

The AHCAM may be prepared by any method known to the art but is preferably made by dissolving the AHCA in aqueous alkali and adding the requisite amount of formaldehyde optionally in the presence of an amine. The AHCAM can then be conveniently isolated by neutralisation and separated in conventional manner for example by filtration. The solubility of the AHCA in aqueous alkali can be increased where necessary by including a water-miscible co-solvent. However, this is not generally necessary.

The amount of formaldehyde used is preferably between 1.0 and 1.10 moles based on the molar concentration of the AHCA for each methylene group inserted into the AHCA When the reaction is carried out in the presence of an amine of formula $HNR^1R^2$ as under typical Mannich reaction conditions the amount of the amine is preferably the same as the molar concentration of formaldehyde.

The reaction is very facile and is preferably carried out at a temperature below 100° C. and especially below 80° C. Preferred temperatures are above 20° C., more preferably above 30° C. and especially above 50° C.

Examples of suitable AHCA are salicylic acid, 5-methyl-, 5-tertbutyl, 5-nonyl- and 5-dodecyl salicylic acid. Examples of suitable AHC containing a fused ring are 2-hydroxy-3-naphthoic including the 5-tertbutyl and 5,7-ditert. butyl derivatives, 2-hydroxy-1-naphthoic, 1-hydroxy-2-naphthoic and 8-hydroxy-1-naphthoic acids.

Examples of suitable amines of formula $HNR^1R^2$ are N-methyl ethylamine, N,N-diethylamine, N,N-dibutylamine, N,N-dihexylamine, N-methyl-2-ethylhexylamine, N-methyl-2-ethylbutylamine N,N-diethanolamine and N-methyl-ethanolamine.

When $R^3$ is other than hydrogen, the AHCAM of formula 1 is preferably made by reacting the AHCAM of formula 1 wherein R is H with an appropriate alkyl or aralkyl halide, especially a bromide, in a suitable liquid in the presence of a base. Preferably, the liquid is water optionally containing a water-miscible solvent and preferred bases are alkali-metal hydroxides such as sodium and potassium hydroxide.

The metal salts or complexes are typically made by dissolving the AHCAM in aqueous alkali and adding an aqueous solution of the desired inorganic metal salt. Typically the inorganic metal salt is a chloride, nitrate or sulphate. The metal salt or complex generally separates from the aqueous alkaline solution and can be isolated by standard methods such as filtration.

It will be readily apparent that the metal salt or complex can be produced in situ without the need to first isolate the AHCAM.

The preferred metals are Mg(II), Ba(II), Fe(III), Al(III) and especially Zn(II) which are typically used as their chloride salt. Zn(II) can also be added as its sulphate.

As noted hereinbefore, the AHCAM including the salt or metal complex thereof can be used as a CCA.

According to a further aspect of the invention there is provided the use of a AHCAM, including salts and metal complexes thereof as a CCA with the exception of pamoic acid.

Useful effects have been obtained with the 2:1 metal salt or complex of 4-hydroxymethyl-3-hydroxy-2-naphthoic acid with zinc or calcium; the 2:1 metal salt or complex of 4-(N-methyl-N-hydroxyethyl)aminomethyl-3-hydroxy-2-naphthoic acid with zinc and the 3:1 iron complex of 4-(N-methyl-N-hydroxyethyl)aminomethyl-3-hydroxy-2-naphthoic acid.

The invention is further illustrated by the following examples wherein all references are to parts by weight unless indicated to the contrary.

EXAMPLE 1

Preparation of 4-hydroxymethyl-3-hydroxy-2-naphthoic acid 3-hydroxy-2-naphthoic acid (60.8 parts, 0.33M, ex Aldrich) was stirred in 400 mls water. Concentrated sodium hydroxide solution (56 parts containing 47% sodium hydroxide, 0.66M) was added and the acid dissolved by heating to about 70° C. This solution was then cooled to 10–12° C. and 37% aqueous formaldehyde (31 parts; 0.38M) was added rapidly.

After stirring for a further 3 hours at 14–16° C. the reaction mass was discharged into ice/water (500 parts) and the pH adjusted to about 3.5 by addition of strong sulphuric acid when the product separated. This was isolated by filtration, washed with water and dried. Yield=71.6 parts (98% theory) mp 285–95° C.

Elemental analysis: $C_{12}H_{10}O_4$ (0.5 $H_2O$) requires 63.4%C, 4.8%H; Found 63.4%C, 4.7%H;

Proton NMR: ($D_2O$/DMSO) δ 5.0 (s, 24, —$CH_2O$—); 7.4–8.5(m, 5H, aromatic)

EXAMPLE 2

Preparation of the 2:1 zinc salt of 4-hydroxymethyl-3-hydroxy-2-naphthoic acid 4-hydroxymethyl-3-hydroxy-2-naphthoic acid (2.18 parts; 0.01M; ex Example 1) was stirred in water (7 parts) containing sodium hydrogen carbonate (0.84 parts; 0.01M). After cooling to 18–24° C., a small amount of 2N sodium carbonate solution was added to adjust the pH to 8.8–9.0 whereupon the acid dissolved.

A solution of zinc sulphate heptahydrate (2 parts; ex Aldrich) in water (4 parts) was slowly added and the reaction stirred for a further 1 hour at 18–24° C. A pale cream suspension was immediately formed and was filtered, washed with water and dried.

Yield=1.69 parts (62.7% theory) mp>300° C. This is CCA 1.

Elemental analysis: Found 53.4%C, 3.4%H, 12.30%Zn; $(C_{12}H_9O_4)_2Zn$(2.2 $H_2O$) requires 53.4%C; 4.2%H; 12.1% Zn.

EXAMPLE 3

Preparation of 4-(N-methyl-N-hydroxyethyl) aminomethyl-3-hydroxy-2-naphthoic acid 3-hydroxy-2-naphthoic acid (18.8 parts, 0.1M, ex Aldrich), water (50 ml) and N-methylethanolamine (12.8 parts, 0.17M, ex Fluka) were stirred together at 20–25° C. to give a clear solution. After heating to 80° C., formaldehyde (10 mls at 37/40% strength by volume, 0.1M ex FSA labs) was added over 10 minutes with stirring at 80–85° C.

After stirring for a further 3 hours at 80–85° C., the reactants were cooled and the pH of the solution adjusted to pH 3–4 by addition of 2M sulphuric acid solution whereupon the product separated as an off-white solid. This was filtered, washed with water and dried.

Yield=23.6 parts (86% theory) mp 127–129° C.

Elemental analysis Found 61.4%C, 6.5%H, 4.7%N; $C_{15}H_{17}NO_4$ requires 65.4%C, 6.2%H, 5.1%N

EXAMPLE 4

Preparation of the 2:1 salt or complex of 4-(N-methyl-N-hydroxyethyl) aminomethyl-3-hydroxy-2-naphthoic acid with zinc The naphthoic acid from Example 3 (22.02 parts, 0.08M) was stirred at 50–60° C. in water (175 mls) containing sodium hydroxide (3.2 parts, 0.08M) to dissolve the acid. A solution of zinc chloride (5.45 parts, 0.04M) in water (8mls) was then added at 50–60° C. whereupon the zinc salt or complex immediately separated. After cooling to 20–25° C., the product was filtered, washed with water and dried.

Yield=20.58 parts (84% theory) mp>250° C. This is CCA 2.

Elemental analysis was consistent with the required product as the trihydrate.

EXAMPLES 5 and 6

Preparation and evaluation as CCA

A styrene/acrylic resin (300 parts, Almacryl B-1500 ex Image Polymers Europe) and CCA (7.5 parts) were melt kneaded at 160–180° C. for 60 minutes. The resulting toner was then cooled, crushed and finally ground by ball-milling until an average particle size between 5 and 25μ was obtained.

The milled toner (0.4 parts) was then mixed with an uncoated iron powder carrier (19.6 parts, RAV-270 ex Powder Tech Corporation, Valparaiso, Ind., USA) in an aluminium tin for 30 minutes on a roller mill.

The resulting CCA was then evaluated using a Toshiba TB 200 blow-off apparatus and the tribo-harge measured after various time intervals. The results are given in Table 1 below.

TABLE 1

| | | Tribo-charge ($\mu Cg^{-1}$) after time(mins) | | | |
|---|---|---|---|---|---|
| Example | CCA | 5 | 10 | 20 | 30 |
| 5 | 1 (Ex 2) | −18 | −21 | −26 | −29 |
| 6 | 2 (Ex 4) | ND | −19 | −21 | −24 |

Footnote to Table 1 ND=not determined

EXAMPLE 7

Preparation of the 3:1 iron salt of 4-(N-methyl-N-2-hydroxyethyl)aminomethyl-3-hydroxy-2-naphthoic acid Ferric chloride hexahydrate (13.52 parts ex Fisons; 0.05M) was dissolved in water with stirring at 50 to 55° C. The naphthoic acid (39.15 parts, 0.142M) as prepared in Example 3 was added and immediately dissolved giving a very dark solution. 2N Sodium hydroxide solution (255 ml) was added in portions with stirring at 55 to 60° C. to give a pH of about 4.25 when a dark brown precipitate gradually formed. The pH was then adjusted to about pH 6 by stirring at 20 to 25° C. with addition of 2N sodium hydroxide solution. The resulting brown solid was filtered, dissolved in hot methanol (600 mls) and the solution screened. After evaporation of the methanol the product was obtained as a dark-brown solid (39.15 parts).

Elemental analysis

Theory: 61.5% C, 5.5% H, 4.8% N, 6.4% Fe;

Found: 56.7% C, 5.0% H, 4.4% N, 6.0% Fe.

The sample contained 1.4% (w/w) water as determined by drying to constant weight at 60° C. and 0.2% (w/w) bound water as determined by Karl Fischer titration. This corresponds to a 92.2% (w/w) strength for the iron salt.

The iron salt was formulated as a toner by the method described in Examples 5 and 6 and the tribo electric charge measured using a Toshiba TB 200 blow-off apparatus. The tribocharge ($\mu Cg^{-1}$) after 5,10,20 and 30 minutes was found to be −17.51, −21.80, −25.91 and −27.04 respectively.

EXAMPLE 8

Preparation of the 2:1 calcium salt of 4-(N-methyl-N-hydroxyethyl)aminomethyl-3-hydroxy-2-naphthoic acid The naphthoic acid prepared as described in Example 3 (13.75 parts, 0.05M) was dissolved in water (100 ml) containing sodium hydroxide (2 parts, 0.05M) by stirring at 20 to 25° C. The solution was heated to 55 to 60° C. and a solution of calcium chloride dihydrate (3.78 parts, 0.025M) dissolved in water (5 ml) was added dropwise over 10 minutes. After stirring for a further 30 minutes at 55–60° C., the reaction mix was allowed to cool and the product filtered, washed with water and dried. The calcium salt was obtained as a bright yellow solid (10.91 parts) mp>300° C. Elemental analysis Theory: 61.2% C, 5.4% H, 4.8% N, 6.8% Ca;

Found: 56.7% C, 6.2% H, 4.1% N, 7.2% Ca

The solid was found to contain 5.5% (w/w) water by Karl Fischer titration.

EXAMPLE 9

Preparation of the 2:1 calcium salt of 4-hydroxymethyl-3-hydroxy-2-naphthoic acid The naphthoic acid prepared as described in Example 1 (21.8 parts, 0.1M) was dissolved in water (150 ml) containing sodium hydroxide (4 parts, 0.1M) with stirring at 15 to 20° C. Calcium chloride dihydrate (7.35 parts, 0.05M) dissolved in water (10 ml) was added dropwise over 10 minutes with stirring at 15 to 20° C. After stirring for a further 60 minutes, the resultant solid was filtered, washed with water and dried at 20 to 25° C. over anhydrous calcium chloride under reduced pressure. Yield=3.0 parts, mp>300° C.

Elemental analysis

Theory: 60.7% C, 3.8% H, 8.5% Ca;

Found: 55.4% C, 3.9% H, 9.2% Ca

The solid was found to contain 8.4% (w/w) bound water by Karl Fischer titration.

We claim:

1. A toner comprising solid particles having a mean diameter of less than 20 microns, which comprise a thermoplastic toner resin and an aromatic carbocyclic hydroxy carboxylic acid having at least one methylene group substituted by hydroxy or optionally substituted amino including salts and metal complexes thereof.

2. A toner as claimed in claim 1 wherein the carboxylic acid group is attached to a carbon atom adjacent to that carrying the hydroxy group in the aromatic carbocyclic hydroxy carboxylic acid.

3. A toner as claimed in claim 1, where the aromatic carbocyclic hydroxy carboxylic acid is a compound of Formula 1:

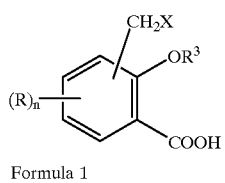

Formula 1 or salt or metal complex thereof; where

X is hydroxy, or —$NR^1R^2$

R is halogen, hydroxy, nitro, carboxy, nitrile, optionally substituted $C_{1-18}$ hydrocarbyl, or two adjacent groups R together with the carbon atoms to which they are attached form an optionally substituted 5- or 6-membered fused ring;

n is 0 to 3;

$R^1$ and $R^2$ is each, independently, hydrogen, optionally substituted $C_{1-18}$ hydrocarbyl or $R^1$ and $R^2$ together with the nitrogen atom to which they are attached form a ring; and $R^3$ is hydrogen, aralkyl or optionally substituted $C_{1-18}$ alkyl.

4. A toner as claimed in claim 3 wherein $R^1$ and $R^2$ are not both hydrogen.

5. A toner as claimed in claim 3 wherein two adjacent groups R form an optionally substituted fused phenyl ring.

6. A toner as claimed in claim 3 wherein $R^3$ is hydrogen.

7. A toner as claimed in claim 1 or claim 3 wherein the aromatic carbocyclic hydroxy carboxylic acid compound of claim 1 or the compound of formula (1) of claim 3 is a salt or complex of a metal selected from group 1a, 2a, 3a, 1b, 2b, 6b, 7b, or 8 of the Periodic Table.

8. A toner as claimed in claim 7 wherein the metal is zinc, calcium or iron.

9. A toner as claimed in claim 1 which further comprises a colorant.

10. A compound selected from the group consisting of:

the 2:1 salt of 4-(N-methyl-N-hydroxyethyl) aminomethyl-3-hydroxy-2-naphthoic acid and zinc;

the 2:1 salt of 4-(N-methyl-N-hydroxyethyl) aminomethyl-3-hydroxy-2-naphthoic acid and calcium; and the 3:1 salt of 4-(N-methyl-N-hydroxyethyl) aminomethyl-3-hydroxy-2-naphthoic acid and iron.

11. A method for improving the tribo-electric charge characteristics of a toner for electroreprographic image processes, comprising:

preparing a toner resin composition by mixing
i) a thermoplastic resin, and
ii) from 0.1% to 12% by weight, based on the total weight of the toner resin composition, of an aromatic carbocyclic hydroxy carboxylic acid having at least one methylene group substituted by hydroxy or optionally substituted amino including salts and metal complexes thereof;

kneading said mixture;

cooling said kneaded mixture;

crushing the cooled mixture; and micronizing the crushed mixture to obtain a toner comprising solid particles having a mean diameter of less than 20 microns.

12. A process for making an electroreprographic image comprising:

developing a latent electrostatic image with a toner comprising a thermoplastic toner resin and a negative charge control agent wherein the negative charge control agent is an aromatic carbocyclic hydroxy carboxylic acid having at least one methylene group substituted by hydroxy or optionally substituted amino including salts and metal complexes thereof.

* * * * *